United States Patent
Nelson et al.

(10) Patent No.: US 8,426,608 B2
(45) Date of Patent: *Apr. 23, 2013

(54) PROCESS FOR PREPARATION OF HIGH MOLECULAR WEIGHT MOLYBDENUM SUCCINIMIDE COMPLEXES

(75) Inventors: Kenneth D. Nelson, Napa, CA (US); James J. Harrison, Novato, CA (US); Paula Rogers, Pinole, CA (US); Mitra Hosseini, Dublin, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 13/011,520

(22) Filed: Jan. 21, 2011

(65) Prior Publication Data

US 2012/0190864 A1    Jul. 26, 2012

(51) Int. Cl.
*C07D 207/404* (2006.01)

(52) U.S. Cl.
USPC .......................................................... 548/402

(58) Field of Classification Search .................. 548/402
See application file for complete search history.

(56) References Cited

U.S. PATENT DOCUMENTS

| | | | |
|---|---|---|---|
| 3,036,003 A | 5/1962 | Verdol et al. | |
| 3,172,892 A | 3/1965 | Le Sner et al. | |
| 3,219,666 A | 11/1965 | Norman et al. | |
| 3,272,746 A | 9/1966 | Le Sner et al. | |
| 3,275,554 A | 9/1966 | Wagenaar | |
| 3,329,658 A | 7/1967 | Fields | |
| 3,438,757 A | 4/1969 | Honnen et al. | |
| 3,449,250 A | 6/1969 | Fields | |
| 3,454,555 A | 7/1969 | Van Der Voort et al. | |
| 3,565,804 A | 2/1971 | Honnen et al. | |
| 3,586,629 A | 6/1971 | Otto et al. | |
| 3,591,598 A | 7/1971 | Traise et al. | |
| 3,666,730 A | 5/1972 | Coleman | |
| 3,980,569 A | 9/1976 | Pindar et al. | |
| 4,234,435 A | 11/1980 | Meinhardt et al. | |
| 4,259,194 A | 3/1981 | deVries et al. | |
| 4,265,773 A | 5/1981 | deVries et al. | |
| 4,283,295 A | 8/1981 | deVries et al. | |
| 4,285,822 A | 8/1981 | deVries et al. | |
| 4,357,149 A | 11/1982 | West et al. | |
| 4,394,279 A | 7/1983 | Devries et al. | |
| 4,500,439 A | 2/1985 | West et al. | |
| 4,612,132 A | 9/1986 | Wollenberg et al. | |
| 4,746,446 A | 5/1988 | Wollenberg et al. | |
| 4,971,598 A | 11/1990 | Andress et al. | |
| 5,716,912 A | 2/1998 | Harrison et al. | |
| 6,165,235 A | 12/2000 | Kolp et al. | |
| 6,372,696 B1 | 4/2002 | Tipton | |
| 6,440,905 B1 | 8/2002 | Epps et al. | |
| 6,962,896 B2 | 11/2005 | Ruhe, Jr. et al. | |
| 2005/0209111 A1 | 9/2005 | Ruhe, Jr. et al. | |
| 2007/0123437 A1 | 5/2007 | Boffa et al. | |
| 2009/0325833 A1 | 12/2009 | Nelson et al. | |

FOREIGN PATENT DOCUMENTS

| | | |
|---|---|---|
| EP | 1371716 | 12/2003 |
| RU | 2201433 | 3/2003 |
| WO | WO2010002863 | 1/2010 |

OTHER PUBLICATIONS

PCT International Search Report, PCT/US2012/020614, filed Jan. 9, 2012, Mail Date: Aug. 3, 2012.

*Primary Examiner* — Shawquia Young
(74) *Attorney, Agent, or Firm* — Carlton Virassammy; Claude J. Caroli

(57) ABSTRACT

Disclosed is a process for preparing a molybdated succinimide complex, the process comprising:
(a) reacting an alkyl or alkenyl mono- or bis-succinimide of a polyamine of formula I or formula II or mixtures thereof:

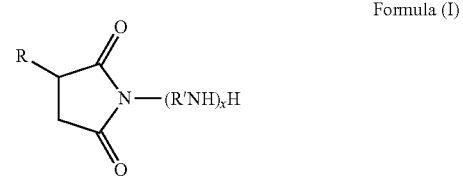

Formula (I)

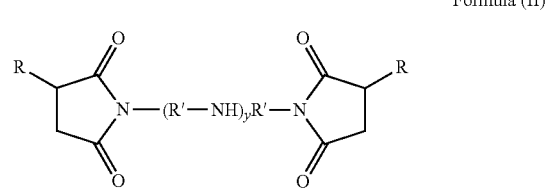

Formula (II)

wherein R is an alkyl or alkenyl group having a number average molecular weight of about 500 to about 5,000, R' is a straight or branched-chain alkylene group having 2 to 3 carbon atoms, x is 2 to 11, and y is 1 to 10, with an α,β-unsaturated mono-carboxylic acid or carboxylic acid ester, in a charge mole ratio of the α,β-unsaturated mono-carboxylic acid or carboxylic acid ester to the succinimide of formula I or formula II or mixtures thereof of greater than 1.05:1 to about 6:1, and wherein the reaction temperature is in the range of from greater than 80° C. to no greater than about 150° C.; and
(b) reacting the succinimide product of step (a) with an acidic molybdenum compound to provide the molybdated succinimide complex, wherein the molybdated succinimide complex is a liquid at room temperature.

32 Claims, No Drawings

PROCESS FOR PREPARATION OF HIGH MOLECULAR WEIGHT MOLYBDENUM SUCCINIMIDE COMPLEXES

FIELD OF THE INVENTION

The present invention generally relates to an improved process for preparing high molecular weight molybdenum succinimide complexes.

BACKGROUND OF THE INVENTION

In general, organic molybdenum compounds are known to improve the lubricating properties of engine oils. For example, molybdenum dithiocarbamates are typically employed for the reduction of friction. The molybdenum dithiocarbamates, however, contain sulfur and slowly lose the ability to reduce friction unless an alternate sulfur source is present in the lubricating oil. Another example of organic molybdenum compounds are sulfurized molybdenum polyisobutenyl succinimide complexes which are used to mediate wear, reduce friction, and/or control oxidation. See, e.g., U.S. Pat. Nos. 4,259,194; 4,265,773; 4,283,295; 4,285,822; and 6,962,896 and U.S. Patent Application Publication No. 2005/0209111. Problems associated with the use of sulfur in lubricating oils are that sulfur can be incompatible with emission control devices and can result in corrosion problems.

U.S. Pat. Nos. 4,357,149 and 4,500,439 disclose molybdated $C_{15}$-$C_{20}$ alkenyl succinimides. In Example XI of both of these patents, a molybdated succinimide is prepared by reacting a $C_{15}$-$C_{20}$ alkenyl succinic anhydride with triethylene tetramine followed by treatment with a molybdic acid solution.

Russian Patent No. 2201433 discloses a molybdated succinimide post-treated with maleic anhydride as an additive for motor oils used in internal combustion engines. Russian Patent No. 2201433 further discloses that the additives are prepared by reacting an alkenyl succinimide of polyethylene polyamine with ammonium molybdate in the presence of water as a promoter and then reacting the resulting product with maleic anhydride taken in amounts of 0.2 to 1.0 mole per 1 mole of alkenyl succinimide of polyethylene polyamine. All of the examples disclosed in Russian Patent No. 2201433 employ a high molecular weight polyisobutenyl (950 M.W.) succinic anhydride (PIBSA) in preparing the alkenyl succinimide of polyethylene polyamine.

Molybdenum succinimide complexes are also described in U.S. Patent Application Publication No. 2009/0325833. These complexes when derived from high molecular weight alkylamines exhibit good friction, wear and oxidation inhibition. These complexes are prepared by post-treating the amine portion of the succinimide with maleic anhydride, at a charge mole ratio of maleic anhydride to succinimide of about 1:1, followed by a further post-treatment with molybdenum trioxide.

SUMMARY OF THE INVENTION

In accordance with one embodiment of the present invention, there is provided a process for preparing a molybdated succinimide complex, the process comprising:

(a) reacting an alkyl or alkenyl mono- or bis-succinimide of a polyamine of formula I or formula II or mixtures thereof:

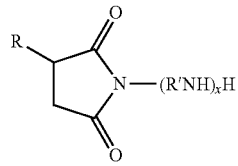
Formula (I)

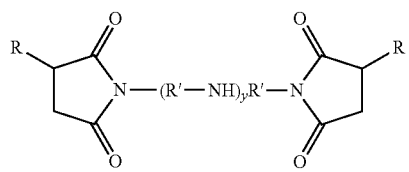
Formula (II)

wherein R is an alkyl or alkenyl group having a number average molecular weight of about 500 to about 5,000, R' is a straight or branched-chain alkylene group having 2 to 3 carbon atoms, x is 1 to 11, and y is 1 to 10, with an α,β-unsaturated mono-carboxylic acid or carboxylic acid ester, in a charge mole ratio of the α,β-unsaturated mono-carboxylic acid or carboxylic acid ester to the succinimide of formula I or formula II or mixtures thereof of greater than 1.05:1 to about 6:1, and wherein the reaction temperature is in the range of from greater than 80° C. to no greater than about 150° C.; and (b) reacting the succinimide product of step (a) with an acidic molybdenum compound to provide the molybdated succinimide complex, wherein the molybdated succinimide complex is a liquid at room temperature.

Among other factors, the present invention is based on the surprising discovery of an improved molybdated succinimide complex and an improved process for its preparation. It has been found that molybdenum succinimide complexes derived from high molecular weight alkyl or alkenyl succinimides where the amine portion of the molecule has been post-treated with an α,β-unsaturated mono-carboxylic acid or carboxylic acid ester results in a product that exhibits low friction and wear.

Another advantage of the present process is that the reaction of an alkyl or alkenyl succinimide of a polyamine with an α,β-unsaturated mono-carboxylic acid or carboxylic acid ester can be carried out at a temperature no greater than about 150° C.

The post-treatment with an α,β-unsaturated mono-carboxylic acid or carboxylic acid ester at no greater than about 150° C. advantageously allows for a product which has improved friction reduction when incorporated into a lubricating oil composition and used in an internal combustion engine.

It has been further discovered that when the charge mole ratio of the α,β-unsaturated mono-carboxylic acid or carboxylic acid ester to the succinimide of formula I or formula II or mixtures thereof is from greater than 1.05:1 to about 6:1, the resulting product exhibits surprisingly improved wear performance over those that have been post-treated where the charge mole ratio of the α,β-unsaturated mono-carboxylic acid or carboxylic acid ester to the succinimide of formula I or formula II or mixtures thereof is about 1:1.

DETAILED DESCRIPTION OF THE INVENTION

In general, provided is a process for preparing a molybdated succinimide complex, the process comprising:

(a) reacting an alkyl or alkenyl mono- or bis-succinimide of a polyamine of formula I or formula II or mixtures thereof:

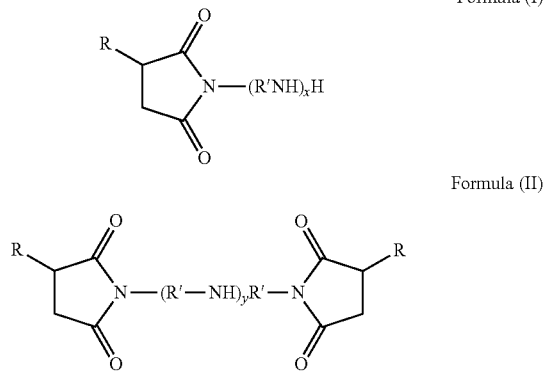

Formula (I)

Formula (II)

wherein R is an alkyl or alkenyl group having a number average molecular weight of about 500 to about 5,000, R' is a straight or branched-chain alkylene group having 2 to 3 carbon atoms, x is 1 to 11, and y is 1 to 10, with an α,β-unsaturated mono-carboxylic acid or carboxylic acid ester, in a charge mole ratio of the α,β-unsaturated mono-carboxylic acid or carboxylic acid ester to the succinimide of formula I or formula II or mixtures thereof of greater than 1.05:1 to about 6:1, and wherein the reaction temperature is in the range of from greater than 80° C. to no greater than about 150° C.; and (b) reacting the succinimide product of step (a) with an acidic molybdenum compound to provide the molybdated succinimide complex, wherein the molybdated succinimide complex is a liquid at room temperature.

In one embodiment, the reaction temperature of step (a) in the process is in the range of from greater than 80° C. to no greater than about 140° C. In another embodiment, the reaction temperature of step (a) in the process is in the range of from greater than 80° C. to no greater than about 135° C.

In one embodiment, the R substituent is an alkyl or alkenyl group having a number average molecular weight of about 500 to about 5,000. In another embodiment, the R substituent is an alkyl or alkenyl group having a number average molecular weight from about 700 to about 2500. In another embodiment, the R substituent is an alkyl or alkenyl group having a number average molecular weight from about 710 to about 1100. In another embodiment, R' is 2; x is 2 to 5; and y is 1 to 4.

In step (a), a succinimide of formula I or formula II or mixtures thereof:

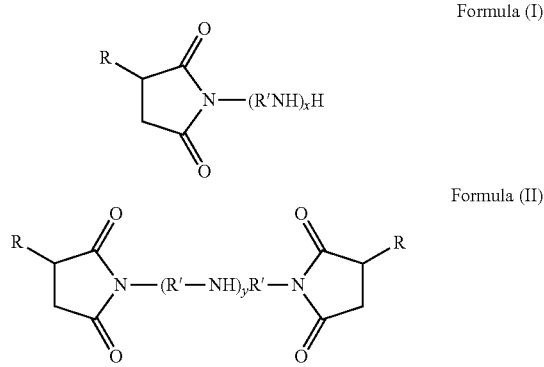

Formula (I)

Formula (II)

wherein R, R', x and y have the aforestated meanings, is reacted with an α,β-unsaturated mono-carboxylic acid or carboxylic acid ester, such as acrylic acid. The starting succinimide of formula I or formula II can be obtained by reacting an anhydride of formula III:

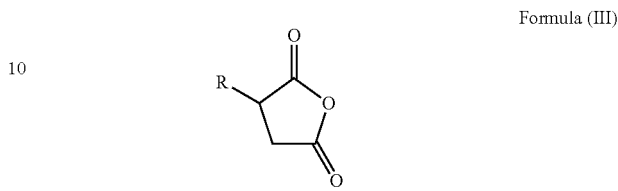

Formula (III)

wherein R has the aforestated meaning, with a polyamine. The anhydride of formula III is either commercially available from such sources as, for example, Chevron Oronite Company LLC, or can be prepared by any method well known in the art. In one embodiment, the charge mole ratio of polyamine to the anhydride of formula III is 0.5:1 to 1:1. In another embodiment, the charge mole ratio of polyamine to the anhydride of formula III is 0.8:1 to 1:1. In another embodiment, the charge mole ratio of polyamine to the anhydride of formula III is 0.9:1.

In one embodiment, the alkyl or alkenyl mono- or bis-succinimide of step (a) is a mixture of the succinimides of formula I and formula II. In another embodiment, the ratio of the mono-succinimide of formula I to the bis-succinimide of formula II in the succinimide mixture is from about 1:1 to 10:1. In another embodiment, the ratio of the mono-succinimide of formula I to the bis-succinimide of formula II in the succinimide mixture is at least about 4:1. In another embodiment, the ratio of the mono-succinimide of formula I to the bis-succinimide of formula II in the succinimide mixture is 9:1. In another embodiment, the ratio of the mono-succinimide of formula I to the bis-succinimide of formula II in the succinimide mixture is 1:1.

Suitable polyamines for use in preparing the succinimide of formula I or formula II are polyalkylene polyamines or mixtures of polyalkylene polyamines, including polyalkylene diamines. Such polyalkylene polyamines will typically contain about 2 to about 12 nitrogen atoms and about 2 to 24 carbon atoms. Particularly suitable polyalkylene polyamines are those having the formula: $H_2N-(R^1NH)_x-H$ wherein $R^1$ is a straight- or branched-chain alkylene group having 2 or 3 carbon atoms, preferably 2 carbon atoms, and x is 2 to 11. Representative examples of suitable polyalkylene polyamines include polyethylene polyamines such as ethylenediamine, diethylenetriamine, triethylenetetraamine, tetraethylenepentamine and mixtures thereof. In one embodiment, the polyalkylene polyamine is tetraethylenepentamine.

Many of the polyamines suitable for use in the present invention are commercially available and others may be prepared by methods which are well known in the art. For example, methods for preparing amines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volume 2, pp. 99 116.

In one embodiment, the anhydride of formula III is reacted with the polyamine at a temperature of about 130° C. to about 220° C. In another embodiment, the anhydride of formula III is reacted with the polyamine at a temperature from about 145° C. to about 175° C. The reaction can be carried out under an inert atmosphere, such as nitrogen or argon. The amount of anhydride of formula III employed in the reaction can range from about 30 to about 95 wt. % and preferably from about 40 to about 60 wt. %, based on the total weight of the reaction mixture. The reaction mixture may be mixed with or without diluent oil. The charge mole ratio (CMR) of polyamine:anhydride of formula III will vary, for example from 0.5:1 to 1:1. In another embodiment, the ratio is 0.8:1 to 1:1. In another embodiment, the ratio is 0.9:1. In another embodiment, the ratio is 0.5:1.

Suitable $\alpha,\beta$-unsaturated mono-carboxylic acids or carboxylic acids esters include, but are not limited to, acrylic acid, methacrylic acid, methyl, ethyl, isopropyl, n-butyl and isobutyl esters of both acrylic and methacrylic acids, and the like, and mixtures thereof. A preferred $\alpha,\beta$-unsaturated mono-carboxylic acid is acrylic acid. This $\alpha,\beta$-unsaturated mono-carboxylic acid or carboxylic acid ester bonds onto an amine portion of the succinimide starting compound to provide a carboxylic acid or ester functionality. The treatment of the succinimide of formula I or formula II or mixtures thereof with the $\alpha,\beta$-unsaturated mono-carboxylic acid advantageously allows for a sufficient amount of the molybdenum compound to be incorporated into the molydbated succinic complex.

Generally, the $\alpha,\beta$-unsaturated mono-carboxylic acid is a liquid at room temperature and does not require heating prior to mixing with the succinimide of formula I or formula II or mixtures thereof. The mole ratio of the $\alpha,\beta$-unsaturated mono-carboxylic acid or carboxylic acid ester, such as acrylic acid, to the succinimide of formula I or formula II or mixtures thereof will vary widely, for example, from greater than 1.05:1 to about 6:1. In another embodiment the molar ratio is from 2:1 to 6:1. In another embodiment the molar ratio is from 1.5:1 to 4:1. In another embodiment the molar ratio is 2:1. In another embodiment the molar ratio is 6:1.

In step (a), the $\alpha,\beta$-unsaturated mono-carboxylic acid or carboxylic acid ester is typically reacted with the succinimide of formula I or formula II or mixtures thereof at a reaction temperature of from greater than 80° C. to no greater than about 150° C. In another embodiment, the reaction temperature is at least 90° C. In another embodiment, the reaction temperature is at least 100° C. In another embodiment, the reaction temperature is at least 120° C. In another embodiment, the reaction temperature is no greater than 140° C. In another embodiment, the reaction temperature is no greater than 135° C.

The molybdenum compounds used to prepare the molybdated succinimide complex of the present invention are acidic molybdenum compounds or salts of acidic molybdenum compounds. Generally, these molybdenum compounds are hexavalent. Representative examples of suitable molybdenum compounds include, but are not limited to, molybdenum trioxide, molybdic acid, ammonium molybdate, sodium molybdate, potassium molybdate and other alkaline metal molybdates and other molybdenum salts such as hydrogen salts, e.g., hydrogen sodium molybdate, $MoOCl_4$, $MoO_2Br_2$, $Mo_2O_3Cl_6$, or similar acidic molybdenum compounds. In one embodiment, the acidic molybdenum compound is selected from molybdenum trioxide, molybdic acid, ammonium molybdate, and alkali metal molybdates. In another embodiment, the acidic molybdenum compound is molybdenum trioxide.

In step (b), a mixture of the succinimide product of step (a) and acidic molybdenum compound is prepared with or without a diluent. A diluent is used, if necessary, to provide a suitable viscosity for easy stirring. Suitable diluents are lubricating oils and liquid compounds containing only carbon and hydrogen. If desired, ammonium hydroxide may also be added to the reaction mixture to provide a solution of ammonium molybdate.

Generally, the reaction mixture is heated at a temperature less than or equal to about 100° C. and preferably from about 80° C. to about 100° C. until the molybdenum is sufficiently reacted. The reaction time for this step is typically in the range of from about 15 minutes to about 5 hours and preferably from about 1 to about 2 hours. The molar ratio of the molybdenum compound to the succinimide product of step (a) is about 0.1:1 to about 2:1. In another embodiment, the molar ratio of the molybdenum compound to the succinimide product of step (a) is from about 0.5:1 to about 1.5:1. In another embodiment, the molar ratio of the molybdenum compound to the succinimide product of step (a) is about 1:1. Any water present following the reaction of the molybdenum compound and succinimide product of step (a) is removed by heating the reaction mixture to a temperature greater than about 100° C. In another embodiment, any water present following the reaction of the molybdenum compound and succinimide product of step (a) is removed by heating the reaction mixture to a temperature from about 120° C. to about 160° C. or by heating the reaction mixture to a suitable temperature under vacuum.

The Oil of Lubricating Viscosity

The base oil of lubricating viscosity for use in the lubricating oil compositions of this invention is typically present in a major amount, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphonic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base, stocks.

Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

Additional Lubricating Oil Additives

Lubricating oil compositions containing the molybdated succinimide complex prepared by the process of the present invention may also contain other conventional additives for imparting auxiliary functions to give a finished lubricating oil composition in which these additives are dispersed or dissolved. For example, the lubricating oil compositions can be blended with antioxidants, anti-wear agents, ashless dispersants, detergents, rust inhibitors, dehazing agents, demulsifying agents, metal deactivating agents, friction modifiers, antifoaming agents, pour point depressants, co-solvents, package compatibilisers, corrosion-inhibitors, dyes, extreme pressure agents and the like and mixtures thereof. A variety of the additives are known and commercially available. These additives, or their analogous compounds, may be employed for the preparation of the lubricating oil compositions of the invention by the usual blending procedures.

Examples of antioxidants include, but are not limited to, aminic types, e.g., diphenylamine, phenyl-alpha-napthylamine, N,N-di(alkylphenyl) amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic) phenol; and mixtures thereof.

Examples of antiwear agents include, but are not limited to, zinc dialkyldithiophosphates and zinc diaryldithiophosphates, e.g., those described in an article by Born et al. entitled "Relationship between Chemical Structure and Effectiveness of some Metallic Dialkyl- and Diaryl-dithiophosphates in Different Lubricated Mechanisms", appearing in Lubrication Science 4-2 January 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Representative examples of ashless dispersants include, but are not limited to, amines, alcohols, amides, or ester polar moieties attached to a polymer backbone via bridging groups. An ashless dispersant of the present invention may be, for example, selected from oil soluble salts, esters, amino-esters, amides, imides, and oxazolines of long chain hydrocarbon substituted mono and dicarboxylic acids or their anhydrides; thiocarboxylate derivatives of long chain hydrocarbons, long chain aliphatic hydrocarbons having a polyamine attached directly thereto; and Mannich condensation products formed by condensing a long chain substituted phenol with formaldehyde and polyalkylene polyamine.

Carboxylic dispersants are reaction products of carboxylic acylating agents (acids, anhydrides, esters, etc.) comprising at least about 34 and preferably at least about 54 carbon atoms with nitrogen containing compounds (such as amines), organic hydroxy compounds (such as aliphatic compounds including monohydric and polyhydric alcohols, or aromatic compounds including phenols and naphthols), and/or basic inorganic materials. These reaction products include imides, amides, esters, and salts.

Succinimide dispersants are a type of carboxylic dispersant. They are produced by reacting hydrocarbyl-substituted succinic acylating agent with organic hydroxy compounds, or with amines comprising at least one hydrogen atom attached to a nitrogen atom, or with a mixture of the hydroxy compounds and amines. The term "succinic acylating agent" refers to a hydrocarbon-substituted succinic acid or a succinic acid-producing compound, the latter encompasses the acid itself. Such materials typically include hydrocarbyl-substituted succinic acids, anhydrides, esters (including half esters) and halides.

Succinic-based dispersants have a wide variety of chemical structures. One class of succinic-based dispersants may be represented by formula IV:

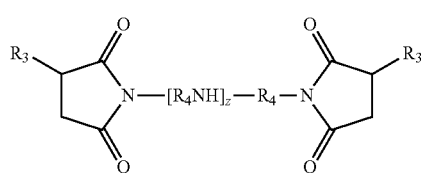

Formula (IV)

wherein each $R_3$ is independently a hydrocarbyl group, such as a polyolefin-derived group. Typically the hydrocarbyl group is an alkenyl group, such as a polyisobutenyl group. Alternatively expressed, the $R_3$ groups can contain about 40 to about 500 carbon atoms, and these atoms may be present in aliphatic forms. $R_4$ is an alkylene group, commonly an ethylene ($C_2H_4$) group; and z is 1 to 11. Examples of succinimide dispersants include those described in, for example, U.S. Pat. Nos. 3,172,892, 4,234,435 and 6,165,235.

The polyalkenes from which the substituent groups are derived are typically homopolymers and interpolymers of polymerizable olefin monomers of 2 to about 16 carbon atoms, and usually 2 to 6 carbon atoms. The amines which are reacted with the succinic acylating agents to form the carboxylic dispersant composition can be monoamines or polyamines.

Succinimide dispersants are referred to as such since they normally contain nitrogen largely in the form of imide functionality, although the nitrogen may be in the form of amines, amine salts, amides, imidazolines as well as mixtures thereof. To prepare a succinimide dispersant, one or more succinic acid-producing compounds and one or more amines are heated and typically water is removed, optionally in the presence of a substantially inert organic liquid solvent/diluent. The reaction temperature can range from about 80° C. up to the decomposition temperature of the mixture or the product, which typically falls between about 100° C. to about 300° C. Additional details and examples of procedures for preparing the succinimide dispersants of the present invention include those described in, for example, U.S. Pat. Nos. 3,172,892, 3,219,666, 3,272,746, 4,234,435, 6,165,235 and 6,440,905.

Suitable ashless dispersants may also include amine dispersants, which are reaction products of relatively high molecular weight aliphatic halides and amines, preferably polyalkylene polyamines. Examples of such amine dispersants include those described in, for example, U.S. Pat. Nos. 3,275,554, 3,438,757, 3,454,555 and 3,565,804.

Suitable ashless dispersants may further include "Mannich dispersants," which are reaction products of alkyl phenols in which the alkyl group contains at least about 30 carbon atoms with aldehydes (especially formaldehyde) and amines (especially polyalkylene polyamines). Examples of such dispersants include those described in, for example, U.S. Pat. Nos. 3,036,003, 3,586,629, 3,591,598 and 3,980,569.

Suitable ashless dispersants may also be post-treated ashless dispersants such as post-treated succinimides, e.g., post-treatment processes involving borate or ethylene carbonate as disclosed in, for example, U.S. Pat. Nos. 4,612,132 and 4,746, 446; and the like as well as other post-treatment processes. The carbonate-treated alkenyl succinimide is a polybutene succinimide derived from polybutenes having a molecular weight of about 450 to about 3000, preferably from about 900 to about 2500, more preferably from about 1300 to about 2400, and most preferably from about 2000 to about 2400, as well as mixtures of these molecular weights.

A preferred ashless dispersant is prepared by reacting, under reactive conditions, a mixture of a polybutene succinic acid derivative, an unsaturated acidic reagent copolymer of an unsaturated acidic reagent and an olefin, and a polyamine, such as disclosed in U.S. Pat. No. 5,716,912, the contents of which are incorporated herein by reference.

Suitable ashless dispersants may also be polymeric, which are interpolymers of oil-solubilizing monomers such as decyl methacrylate, vinyl decyl ether and high molecular weight olefins with monomers containing polar substituents. Examples of polymeric dispersants include those described in, for example, U.S. Pat. Nos. 3,329,658; 3,449,250 and 3,666,730.

In one preferred embodiment of the present invention, an ashless dispersant for use in the lubricating oil composition is a bis-succinimide derived from a polyisobutenyl group having a number average molecular weight of about 700 to about 2300. The dispersant(s) for use in the lubricating oil compositions of the present invention are preferably non-polymeric (e.g., are mono- or bis-succinimides).

Generally, the one or more ashless dispersants are present in the lubricating oil composition in an amount ranging from about 0.01 wt. % to about 10 wt. %, based on the total weight of the lubricating oil composition.

Representative examples of metal detergents include sulfonates, alkylphenates, sulfurized alkyl phenates, carboxylates, salicylates, phosphonates, and phosphinates. Commercial products are generally referred to as neutral or overbased. Overbased metal detergents are generally produced by carbonating a mixture of hydrocarbons, detergent acid, for example: sulfonic acid, alkylphenol, carboxylate etc., metal oxide or hydroxides (for example calcium oxide or calcium hydroxide) and promoters such as xylene, methanol and water. For example, for preparing an overbased calcium sulfonate, in carbonation, the calcium oxide or hydroxide reacts with the gaseous carbon dioxide to form calcium carbonate. The sulfonic acid is neutralized with an excess of CaO or $Ca(OH)_2$, to form the sulfonate.

Other examples of suitable detergents include borated sulfonates. In general, a borated sulfonate for use herein can be any borated sulfonate known in the art. A borated sulfonate for use herein can have a total base number (TBN) of from about 10 to about 500. In one embodiment, a borated sulfonate has a TBN is from about 10 to about 100. In one embodiment, a borated sulfonate has a TBN is from about 100 to about 250. In one embodiment, a borated sulfonate has a TBN of from about 250 to about 500.

The borated alkaline earth metal sulfonates can be prepared by methods known in the art, e.g., as disclosed in U.S. Patent Application Publication No. 20070123437, the contents of which are incorporated by reference herein. For example, the borated alkaline earth metal sulfonate is prepared in the following manner: (a) reacting (i) at least one of an oil soluble sulfonic acid or alkaline earth sulfonate salt or mixtures thereof; (ii) at least one source of an alkaline earth metal; and (iii) at least one source of boron, in the presence of (iv) at least one hydrocarbon solvent; and (v) from 0 to less than 10 mole percent, relative to the source of boron, of an overbasing acid, other than the source of boron; and (b) heating the reaction product of (a) to a temperature above the distillation temperature of (iv) to distill (iv) and water of reaction.

Metal-containing or ash-forming detergents function as both detergents to reduce or remove deposits and as acid neutralizers or rust inhibitors, thereby reducing wear and corrosion and extending engine life. Detergents generally comprise a polar head with a long hydrophobic tail. The polar head comprises a metal salt of an acidic organic compound. The salts may contain a substantially stoichiometric amount of the metal in which case they are usually described as normal or neutral salts, and would typically have a total base number or TBN (as can be measured by ASTM D2896) of from 0 to about 80. A large amount of a metal base may be incorporated by reacting excess metal compound (e.g., an oxide or hydroxide) with an acidic gas (e.g., carbon dioxide). The resulting overbased detergent comprises neutralized detergent as the outer layer of a metal base (e.g., carbonate) micelle. Such overbased detergents may have a TBN of about 150 or greater, and typically will have a TBN of from about 250 to about 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., barium, sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from about 20 to about 450, neutral and overbased calcium phenates and sulfurized phenates having TBN of from about 50 to about 450 and neutral and overbased magnesium or calcium salicylates having a TBN of from about 20 to about 450. Combinations of detergents, whether overbased or neutral or both, may be used.

In one embodiment, the detergent can be one or more alkali or alkaline earth metal salts of an alkyl-substituted hydroxyaromatic carboxylic acid. Suitable hydroxyaromatic compounds include mononuclear monohydroxy and polyhydroxy aromatic hydrocarbons having 1 to 4, and preferably 1 to 3, hydroxyl groups. Suitable hydroxyaromatic compounds include phenol, catechol, resorcinol, hydroquinone, pyrogallol, cresol, and the like. The preferred hydroxyaromatic compound is phenol.

The alkyl substituted moiety of the alkali or alkaline earth metal salt of an alkyl-substituted hydroxyaromatic carboxylic acid is derived from an alpha olefin having from about 10 to about 80 carbon atoms. The olefins employed may be linear or branched. The olefin may be a mixture of linear olefins, a mixture of isomerized linear olefins, a mixture of branched olefins, a mixture of partially branched linear or a mixture of any of the foregoing.

In one embodiment, the mixture of linear olefins that may be used is a mixture of normal alpha olefins selected from olefins having from about 12 to about 30 carbon atoms per molecule. In one embodiment, the normal alpha olefins are isomerized using at least one of a solid or liquid catalyst.

In another embodiment, the olefins are a branched olefinic propylene oligomer or mixture thereof having from about 20 to about 80 carbon atoms, i.e., branched chain olefins derived from the polymerization of propylene. The olefins may also be substituted with other functional groups, such as hydroxy groups, carboxylic acid groups, heteroatoms, and the like. In one embodiment, the branched olefinic propylene oligomer or mixtures thereof have from about 20 to about 60 carbon atoms. In one embodiment, the branched olefinic propylene oligomer or mixtures thereof have from about 20 to about 40 carbon atoms.

In one embodiment, at least about 75 mole % (e.g., at least about 80 mole %, at least about 85 mole %, at least about 90 mole %, at least about 95 mole %, or at least about 99 mole %) of the alkyl groups contained within the alkali or alkaline earth metal salt of an alkyl-substituted hydroxyaromatic carboxylic acid such as the alkyl groups of an alkaline earth metal salt of an alkyl-substituted hydroxybenzoic acid detergent are a $C_{20}$ or higher. In another embodiment, the alkali or alkaline earth metal salt of an alkyl-substituted hydroxyaromatic carboxylic acid is an alkali or alkaline earth metal salt of an alkyl-substituted hydroxybenzoic acid that is derived from an alkyl-substituted hydroxybenzoic acid in which the alkyl groups are the residue of normal alpha-olefins containing at least 75 mole % $C_{20}$ or higher normal alpha-olefins.

In another embodiment, at least about 50 mole % (e.g., at least about 60 mole %, at least about 70 mole %, at least about 80 mole %, at least about 85 mole %, at least about 90 mole %, at least about 95 mole %, or at least about 99 mole %) of the alkyl groups contained within the alkali or alkaline earth metal salt of an alkali-substituted hydroxyaromatic carboxylic acid such as the alkyl groups of an alkali or alkaline earth metal salt of an alkyl-substituted hydroxybenzoic acid are about $C_{14}$ to about $C_{18}$.

The resulting alkali or alkaline earth metal salt of an alkyl-substituted hydroxyaromatic carboxylic acid will be a mixture of ortho and para isomers. In one embodiment, the product will contain about 1 to 99% ortho isomer and 99 to 1% para isomer. In another embodiment, the product will contain about 5 to 70% ortho and 95 to 30% para isomer.

The alkali or alkaline earth metal salts of an alkyl-substituted hydroxyaromatic carboxylic acid can be neutral or overbased. Generally, an overbased alkali or alkaline earth metal salt of an alkyl-substituted hydroxyaromatic carboxylic acid is one in which the TBN of the alkali or alkaline earth metal salts of an alkyl-substituted hydroxyaromatic carboxylic acid has been increased by a process such as the addition of a base source (e.g., lime) and an acidic overbasing compound (e.g., carbon dioxide).

Overbased salts may be low overbased, e.g., an overbased salt having a TBN below about 100. In one embodiment, the TBN of a low overbased salt may be from about 5 to about 50. In another embodiment, the TBN of a low overbased salt may be from about 10 to about 30. In yet another embodiment, the TBN of a low overbased salt may be from about 15 to about 20.

Overbased detergents may be medium overbased, e.g., an overbased salt having a TBN from about 100 to about 250. In one embodiment, the TBN of a medium overbased salt may be from about 100 to about 200. In another embodiment, the TBN of a medium overbased salt may be from about 125 to about 175.

Overbased detergents may be high overbased, e.g., an overbased salt having a TBN above about 250. In one embodiment, the TBN of a high overbased salt may be from about 250 to about 450.

Sulfonates may be prepared from sulfonic acids which are typically obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl or their halogen derivatives. The alkylation may be carried out in the presence of a catalyst with alkylating agents having from about 3 to more than 70 carbon atoms. The alkaryl sulfonates usually contain from about 9 to about 80 or more carbon atoms, preferably from about 16 to about 60 carbon atoms per alkyl substituted aromatic moiety.

The oil soluble sulfonates or alkaryl sulfonic acids may be neutralized with oxides, hydroxides, alkoxides, carbonates, carboxylate, sulfides, hydrosulfides, nitrates and borates. The amount of metal compound is chosen having regard to the desired TBN of the final product but typically ranges from about 100 to about 220 wt. % (preferably at least about 125 wt. %) of that stoichiometrically required.

Metal salts of phenols and sulfurized phenols are prepared by reaction with an appropriate metal compound such as an oxide or hydroxide and neutral or overbased products may be obtained by methods well known in the art. Sulfurized phenols may be prepared by reacting a phenol with sulfur or a sulfur containing compound such as hydrogen sulfide, sulfur monohalide or sulfur dihalide, to form products which are generally mixtures of compounds in which 2 or more phenols are bridged by sulfur containing bridges.

Generally, the one or more detergents are present in the lubricating oil composition in an amount ranging from about 0.01 wt. % to about 10 wt. %, based on the total weight of the lubricating oil composition.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids; fatty acid amides, glycerol esters, borated glycerol esters; and fatty imidazolines as disclosed in U.S. Pat. No. 6,372,696, the contents of which are herein incorporated by reference; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine and the like and mixtures thereof.

Examples of antifoaming agents include, but are not limited to, polymers of alkyl methacrylate; polymers of dimethylsilicone and the like and mixtures thereof.

Examples of a pour point depressant include, but are not limited to, polymethacrylates, alkyl acrylate polymers, alkyl methacrylate polymers, di(tetra-paraffin phenol)phthalate, condensates of tetra-paraffin phenol, condensates of a chlorinated paraffin with naphthalene and combinations thereof. In one embodiment, a pour point depressant comprises an ethylene-vinyl acetate copolymer, a condensate of chlorinated paraffin and phenol, polyalkyl styrene and the like and combinations thereof. The amount of the pour point depressant may vary from about 0.01 wt. % to about 10 wt. %.

Examples of a demulsifier include, but are not limited to, anionic surfactants (e.g., alkyl-naphthalene sulfonates, alkyl benzene sulfonates and the like), nonionic alkoxylated alkylphenol resins, polymers of alkylene oxides (e.g., polyethylene oxide, polypropylene oxide, block copolymers of ethylene oxide, propylene oxide and the like), esters of oil soluble acids, polyoxyethylene sorbitan ester and the like and combinations thereof. The amount of the demulsifier may vary from about 0.01 wt. % to about 10 wt. %.

Examples of a corrosion inhibitor include, but are not limited to, half esters or amides of dodecylsuccinic acid, phosphate esters, thiophosphates, alkyl imidazolines, sarcosines and the like and combinations thereof. The amount of the corrosion inhibitor may vary from about 0.01 wt. % to about 5 wt. %.

Examples of an extreme pressure agent include, but are not limited to, sulfurized animal or vegetable fats or oils, sulfurized animal or vegetable fatty acid esters, fully or partially esterified esters of trivalent or pentavalent acids of phosphorus, sulfurized olefins, dihydrocarbyl polysulfides, sulfurized Diels-Alder adducts, sulfurized dicyclopentadiene, sulfurized or co-sulfurized mixtures of fatty acid esters and monounsaturated olefins, co-sulfurized blends of fatty acid, fatty acid ester and alpha-olefin, functionally-substituted dihydrocarbyl polysulfides, thia-aldehydes, thia-ketones, epithio compounds, sulfur-containing acetal derivatives, co-sulfurized blends of terpene and acyclic olefins, and polysulfide olefin products, amine salts of phosphoric acid esters or thiophosphoric acid esters and the like and combinations thereof. The amount of the extreme pressure agent may vary from about 0.01 wt. % to about 5 wt. %.

Each of the foregoing additives, when used, is used at a functionally effective amount to impart the desired properties to the lubricant. Thus, for example, if an additive is a friction modifier, a functionally effective amount of this friction modifier would be an amount sufficient to impart the desired friction modifying characteristics to the lubricant. Generally, the concentration of each of these additives, when used, may range, unless otherwise specified, from about 0.001% to about 20% by weight, and in one embodiment about 0.01% to about 10% by weight based on the total weight of the lubricating oil composition.

The final application of the lubricating oil compositions containing the molybdated succinimide complexes prepared by the process of this invention may be, for example, in marine cylinder lubricants in crosshead diesel engines, crankcase lubricants in automobiles and locomotives and the like, lubricants for heavy machinery such as steel mills and the like, or as greases for bearings and the like. Whether the lubricating oil composition is fluid or solid will ordinarily depend on whether a thickening agent is present. Typical thickening agents include polyurea acetates, lithium stearate and the like.

In another embodiment of the invention, the molybdated succinimide complex prepared by the process of the present invention may be provided as an additive package or concentrate in which the additive is incorporated into a substantially inert, normally liquid organic diluent such as, for example, mineral oil, naphtha, benzene, toluene or xylene to form an additive concentrate. These concentrates usually contain from about 20% to about 80% by weight of such diluent. Typically, a neutral oil having a viscosity of about 4 to about 8.5 cSt at 100° C. and preferably about 4 to about 6 cSt at 100° C. will be used as the diluent, though synthetic oils, as well as other organic liquids which are compatible with the additives and finished lubricating oil can also be used. The additive package will also typically contain one or more of the various other additives, referred to above, in the desired amounts and ratios to facilitate direct combination with the requisite amount of base oil.

EXAMPLES

The following non-limiting examples are illustrative of the present invention.

Example 1

Molybdenum Post-Treated High Molecular Weight Succinimide Complex Made from Acrylic Acid at Low Temperature (CMR of Acrylic Acid to Succinimide=2:1)

Into a round bottom flask equipped with an overhead mechanical stirrer, water condenser with nitrogen line and Dean-Stark trap, addition funnel, temperature controller, heating mantle, and thermocouple was added 200.00 g of a polyisobutenyl succinic anhydride where the polyisobutenyl group had a number average molecular weight of 1000 (PIBSA 1000) (available from Chevron Oronite Company LLC) and 43.35 g of Chevron 100 neutral oil. The mixture was heated to 130° C. and 28.12 g of tetraethylenepentamine (TEPA; 0.9 mole equivalent to PIBSA 1000) was charged drop wise into the mixture via the addition funnel. Slight foaming occurred during the initial charge stage. After the TEPA was charged, the temperature was increased to 165° C. and then held at 165° C. for about 5 hours. The reaction was complete as indicated by the IR spectrum.

The material was cooled to room temperature and 50.80 g was transferred to a round bottom flask. The flask was heated to 74° C. for acrylic acid addition. Next, 2.90 g of acrylic acid (2 mole equivalent to TEPA) was added drop-wise. After addition of acrylic acid, the reactor temperature was increased to 135° C. and then held at this temperature until completion of the reaction (about 3 to 5 hours).

Next, 16.15 g of the acrylic acid treated succinimide was added to a 100 mL 3-neck round bottom flask equipped with a magnetic stir plate, Dean-Stark trap with condenser and nitrogen line. 42.3 g of toluene was added and the mixture was stirred and heated to 65° C. to dissolve. Next, 1.229 g of molybdenum trioxide (1 mole equivalent to TEPA), and 9.63 g of de-ionized water was added. The mixture was stirred and heated at 90° C. overnight. Water and toluene were then removed at 114° C.

The product was cooled and then filtered through Celite 512 and anhydrous magnesium sulfate with a Buchner funnel. The filtrate was collected and concentrated using a rotary evaporator (full pump vacuum at a maximum temperature of 90° C.) to remove toluene and any residual water. The product was a brown liquid at room temperature, and had the following properties:
Mo=4.758 wt. %
Total Base Number=35.9 mg KOH/g Example 2

Molybdenum Post-Treated High Molecular Weight Succinimide Complex Made from Acrylic Acid at Low Temperature (CMR of Acrylic Acid to Succinimide=6:1)

A molybdated succinimide complex was prepared using the same general procedure and components outlined in Example 1 except that 6 mole equivalents of acrylic acid to succinimide was used for the acrylic acid treatment. The molybdated succinimide complex was a brown liquid at room temperature, and had the following properties:
Mo=4.575 wt. %
Total Base Number=44.9 mg KOH/g

Example 3

Molybdenum Post-Treated High Molecular Weight Bis-Succinimide Complex Made from Acrylic Acid at Low Temperature (CMR of Acrylic Add to Succinimide=2:1)

A molybdated succinimide complex was prepared using the same general procedure and components outlined in Example 1 except that 0.5 mole equivalent of TEPA was used to make the succinimide. The molybdated succinimide complex was a brown liquid at room temperature, and had the following properties:
Mo=2.680 wt. %
Total Base Number=25.7 mg KOH/g

Example 4

Molybdenum Post-Treated High Molecular Weight Bis-Succinimide Complex Made from Acrylic Acid at Low Temperature (CMR of Acrylic Acid to Succinimide=6:1)

A molybdated succinimide complex was prepared using the same general procedure and components outlined in Example 2 except that 0.5 mole equivalent of TEPA was used to make the succinimide. The molybdated succinimide complex was a green liquid at room temperature, and had the following properties:
Mo=2.509 wt.
Total Base Number=25.3 mg KOH/g

Comparative Example A

Molybdenum Post-Treated High Molecular Weight Succinimide Complex Made from Acrylic Acid at Low Temperature (CMR of Acrylic Acid to Succinimide=1:1)

Into a round bottom flask equipped with an overhead mechanical stirrer, water condenser with nitrogen line and Dean-Stark trap, addition funnel, temperature controller, heating mantle, and thermocouple was added 100.00 g of a polyisobutenyl succinic anhydride where the polyisobutenyl group had a number average molecular weight of 1000 (PIBSA 1000) (available from Chevron Oronite Company) and 21.8 g of Chevron 100 neutral oil. The mixture was heated to 130° C. and 13.92 g of tetraethylenepentamine (TEPA; 0.9 mole equivalent to PIBSA 1000) was charged drop wise into the mixture via the addition funnel. Slight foaming occurred during the initial charge stage. After the TEPA was charged, the temperature was increased to 165° C. and then held at 165° C. for about 6 hours. The reaction was complete as indicated by the IR spectrum.

The material was cooled to room temperature and 22.83 g was transferred to a round bottom flask. The flask was heated to 40° C. for acrylic acid addition. Next, 0.65 g of acrylic acid (1 mole equivalent to succinimide) was added drop-wise. After addition of acrylic acid, the reactor temperature was increased to 135° C. and then held at this temperature until completion of the reaction (about 3 to 5 hours).

Next, 8.578 g of the acrylic acid treated succinimide was added to a 100 mL 3-neck round bottom flask equipped with a magnetic stir plate, Dean-Stark trap with condenser and nitrogen line. 15.06 g of toluene was added and the mixture was stirred and heated to 65° C. to dissolve. Next, 0.656 g of molybdenum trioxide (1 mole equivalent to the acrylic acid treated succinimide), and 6.14 g of de-ionized water was added. The mixture was stirred and heated at 90° C. overnight. Water and toluene were then removed at 114° C.

The product was cooled and then filtered through Celite 512 and anhydrous magnesium sulfate with a Buchner funnel. The filtrate was collected and concentrated using a rotary evaporator (full pump vacuum at a maximum temperature of 90° C.) to remove toluene and any residual water. The product was a brown liquid at room temperature, and had the following properties:
Mo=4.740 wt. %
Total Base Number=79.9 mg KOH/g

Comparative Example B

Molybdenum Post-Treated High Molecular Weight Bis-Succinimide Complex Made from Acrylic Acid at Low Temperature (CMR of Acrylic Acid to Succinimide=1:1)

A molybdated succinimide complex was prepared using the same general procedure and components outlined in Comparative Example A except that 0.5 mole equivalent of TEPA was used to make the succinmide. The molybdated succinimide complex was a brown liquid at room temperature, and had the following properties:
Mo=2.755 wt. 96
Total Base Number=27.5 mg KOH/g

Example 5

A lubricating oil composition was formed by adding 1 wt. % of the lubricating oil additive of Example 1 to a CHEVRON 100 neutral oil.

Example 6

A lubricating oil composition was formed by adding 1 wt. % of the lubricating oil additive of Example 2 to a CHEVRON 100 neutral oil.

Example 7

A lubricating oil composition was formed by adding 1 wt. % of the lubricating oil additive of Example 3 to a CHEVRON 100 neutral oil.

Example 8

A lubricating oil composition was formed by adding 1 wt. % of the lubricating oil additive of Example 4 to a CHEVRON 100 neutral oil.

Comparative Example C

A lubricating oil composition was formed by adding 1 wt. % of the lubricating oil additive of Comparative Example A to a CHEVRON 100 neutral oil.

Comparative Example D

A lubricating oil composition was formed by adding 1 wt. % of the lubricating oil additive of Comparative Example B to a CHEVRON 100 neutral oil.

Example 9

Wear Performance

Mini-Traction Machine (MTM) Evaluation

The lubricating oil additives of Examples 5 to 8 were evaluated for wear using a Mini-Traction Machine (MTM) tribometer (PCS Instruments Ltd., London UK), and were compared to the wear performance of Comparative Examples C and D. The MTM tribometer was set up to run in pin on disk mode using polished disks of 52100 steel from PCS Instruments, and a 0.25 inch stationary ball bearing, also of 52100 steel from Falex Corporation, in place of a pin. The test was conducted at 100° C. for 40 minutes at 7 Newtons load at a sliding speed of 200 mm/s following a break-in period of 5 minutes at 0.1 Newtons and a sliding speed of 2000 mm/s. The wear scars on the balls were measured manually on an optical microscope and recorded. In this test, the lower the wear scar corresponds to more effective anti-wear performance. The MTM wear performance data are presented in Table 1.

TABLE 1

MTM Wear Performance Results

| Test Oil | Succinimide | CMR (Acrylic Acid:Succinimide) | Wear scar (microns) |
|---|---|---|---|
| Comparative Example C | 0.9, PIBSA/TEPA | 1:1 | 187.4 |
| Example 5 | 0.9, PIBSA/TEPA | 2:1 | 121.6 |
| Example 6 | 0.9, PIBSA/TEPA | 6:1 | 126.5 |
| Comparative Example D | bis, PIBSA/TEPA | 1:1 | 153.8 |
| Example 7 | bis, PIBSA/TEPA | 2:1 | 143.9 |
| Example 8 | bis, PIBSA/TEPA | 6:1 | 123.6 |

As the results illustrated in Table 1 show, the molybdenum succinimide compounds made from a CMR of acrylic acid to succinimide of about 2:1 or about 6:1 (Examples 5 through 8) demonstrate superior anti-wear performance over the molybdenum succinimide compounds made from a CMR of acrylic acid to succinimide of about 1:1 (Comparative Examples C and D).

Example 10

A baseline lubricating oil formulation was formed containing 5 wt. % succinimide dispersant, 3 wt. % borated succinimide dispersant, (4 mM/kg) low overbased calcium sulfonate, (58 mM/kg) carboxylate detergent, (8 mM/kg) zinc dithiophosphate, 0.5 wt. % diphenylamine antioxidant, 0.5 wt. % hindered phenol anti-oxidant, 0.3 wt. % pour point depressant, 9.85 wt. % olefin copolymer viscosity index improver and 5 ppm foam inhibitor in a Group II base oil.

Example 11

A baseline lubricating oil formulation was formed containing the same additives, base oil and treat rate as in EXAMPLE 10. The lubricating oil additive of EXAMPLE 1 was formulated into this baseline lubricating oil such that the total Mo content in the formulation was 500 ppm.

Comparative Example E

Molybdenum Post-Treated High Molecular Weight Succinimide Complex Made from Acrylic Acid at 80° C. (CMR of Acrylic Acid to Succinimide=2:1)

A molybdated succinimide complex was prepared using the same general procedure and components outlined in Example 1 except that the acrylic acid was added dropwise starting at room temperature and the temperature was maintained below 100° C. for the addition of acrylic acid and then a reaction temperature of 80° C. was maintained until the reaction was complete. The molybdated succinimide complex was a greenish brown liquid at room temperature, and had the following properties:
Mo=4.914 wt. %
Total Base Number=56.95 mg KOH/g Comparative Example F A baseline lubricating oil formulation was formed containing the same additives, base oil and treat rate as in EXAMPLE 10. The lubricating oil additive of COMPARATIVE EXAMPLE E was formulated into this baseline lubricating oil such that the total Mo content in the formulation was 500 ppm.

Example 12

Friction Performance

High Frequency Reciprocating Rig (HFRR) Evaluation

The friction performance of the lubricating oil compositions of Examples 10 and 11 was evaluated the High Frequency Reciprocating Rig (HFRR), and compared to the friction performance of the lubricating oil composition of Comparative Example F. The HFRR test rig is an industry recognized tribometer for determining lubricant performance. The PCS instrument uses an electromagnetic vibrator to oscillate a specimen (the ball) over a small amplitude while pressing it against a fixed specimen (a flat disk). The amplitude and frequency of the oscillation and the load are variable. The frictional force between the ball and flat and the electrical contact resistance (ECR) are measured. The flat, stationary specimen is held in a bath to which the lubricating oil is added, and can be heated. For this test, the tribometer was set up to run at 20 Hz for 20 minutes, using 6 mm ball on flat specimens of 52100 steel. The load was 1kg and temperature was 116° C. The lubricating oils were pretreated with about 6% by weight, based on the total weight of lubricating oil, of diesel engine soot collected from diesel engine exhaust. The soot was stirred into the oil to wet it and then homogenized for 15 minutes prior to testing. In this test, a smaller coefficient of friction corresponds to a more effective lubricating additive. The HFRR friction performance data are represented in Table 2.

TABLE 2

HFRR Wear and Friction Performance Results

| Description | Coefficient of Friction |
|---|---|
| Example 10 (Baseline) (No Molybdenum Additive) | 0.123 |
| Comparative Example F (Example 10 + 500 ppm E) | 0.13 |
| Example 11 (Example 10 + 500 ppm Example 1) | 0.078 |

As the data in Table 2 show, the molybdenum succinimide complex of the present invention, derived from acrylic acid at a charge mole ratio of acrylic acid to succinimide of 2:1, and prepared at a temperature in the range of from greater than 80° C. to no greater than 150° C. (Example 11), demonstrates improved anti-friction properties over the corresponding molybdenum succinimide complex derived from acrylic acid at a charge mole ratio of acrylic acid to succinimide of 2:1 and prepared at 80° C. (Comparative Example F).

It will be understood that various modifications, may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A process for preparing a molybdated succinimide complex, the process comprising:
   (a) reacting an alkyl or alkenyl mono- or bis-succinimide of a polyamine of formula I or formula II or mixtures thereof:

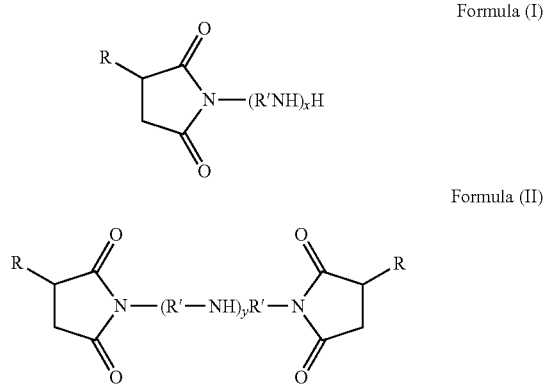

wherein R is an alkyl or alkenyl group having a number average molecular weight of about 500 to about 5,000, R' is a straight or branched-chain alkylene group having 2 to 3 carbon atoms, x is 2 to 11, and y is 1 to 10, with an α,β-unsaturated mono-carboxylic acid or carboxylic acid ester, in a charge mole ratio of the α,β-unsaturated mono-carboxylic acid or carboxylic acid ester to the succinimide of formula I or formula II or mixtures thereof of greater than 1.05:1 to about 6:1, and wherein the reaction temperature is in the range of from greater than 80° C. to no greater than about 150° C.; and
   (b) reacting the succinimide product of step (a) with an acidic molybdenum compound to provide the molybdated succinimide complex, wherein the molybdated succinimide complex is a liquid at room temperature.

2. The process of claim 1, wherein R is an alkyl or alkenyl group having a number average molecular weight of about 700 to about 2,500, R' is an alkylene group having 2 carbon atoms, x is 2 to 5, and y is 1 to 4.

3. The process of claim 1, wherein R is an alkyl or alkenyl group having a number average molecular weight of about 710 to about 1,100, R' is an alkylene group having 2 carbon atoms, x is 2 to 5, and y is 1 to 4.

4. The process of claim 1, wherein the α,β-unsaturated mono-carboxylic acid or carboxylic acid ester is selected from the group consisting of acrylic acid, methacrylic acid and mixtures thereof.

5. The process of claim 1, wherein the acidic molybdenum compound is selected from the group consisting of molybdic acid, ammonium molybdate, sodium molybdate, potassium molybdates, hydrogen sodium molybdate, $MoOCl_4$, $MoO_2Br_2$, $Mo_2O_3Cl_6$, molybdenum trioxide and mixtures thereof.

6. The process of claim 1, wherein the α,β-unsaturated mono-carboxylic acid or carboxylic acid ester is acrylic acid and the acidic molybdenum compound is molybdenum trioxide.

7. The process of claim 2, wherein the α,β-unsaturated mono-carboxylic acid or carboxylic acid ester is acrylic acid and the acidic molybdenum compound is molybdenum trioxide.

8. The process of claim 3, wherein the α,β-unsaturated mono-carboxylic acid or carboxylic acid ester is acrylic acid and the acidic molybdenum compound is molybdenum trioxide.

9. The process of claim 1, wherein the molar ratio of the α,β-unsaturated mono-carboxylic acid or carboxylic acid ester thereof to the succinimide of formula I or formula II or mixtures thereof is about 1.5:1 to about 6:1.

10. The process of claim 1, wherein the molar ratio of the α,β-unsaturated mono-carboxylic acid or carboxylic acid ester thereof to the succinimide of formula I or formula II or mixtures thereof is about 1.5:1 to about 4:1.

11. The process of claim 1, wherein the molar ratio of the α,β-unsaturated mono-carboxylic acid or carboxylic acid ester thereof to the succinimide of formula I or formula II or mixtures thereof is about 2:1.

12. The process of claim 2, wherein the molar ratio of the α,β-unsaturated mono-carboxylic acid or carboxylic acid ester thereof to the succinimide of formula I or formula II or mixtures thereof is about 1.5:1 to about 6:1.

13. The process of claim 2, wherein the molar ratio of the α,β-unsaturated mono-carboxylic acid or carboxylic acid ester thereof to the succinimide of formula I or formula II or mixtures thereof is about 1.5:1 to about 4:1.

14. The process of claim 2, wherein the molar ratio of the α,β-unsaturated mono-carboxylic acid or carboxylic acid ester thereof to the succinimide of formula I or formula II or mixtures thereof is about 2:1.

15. The process of claim 3, wherein the molar ratio of the α,β-unsaturated mono-carboxylic acid or carboxylic acid ester thereof to the succinimide of formula I or formula II or mixtures thereof is about 1.5:1 to about 6:1.

16. The process of claim 3, wherein the molar ratio of the α,β-unsaturated mono-carboxylic acid or carboxylic acid ester thereof to the succinimide of formula I or formula II or mixtures thereof is about 1.5:1 to about 4:1.

17. The process of claim 3, wherein the molar ratio of the α,β-unsaturated mono-carboxylic acid or carboxylic acid ester thereof to the succinimide of formula I or formula II or mixtures thereof is about 2:1.

18. The process of claim 1, wherein the molar ratio of the molybdenum compound to the succinimide product of step (a) is about 0.1:1 to about 2:1.

19. The process of claim 1, wherein the molar ratio of the molybdenum compound to the succinimide product of step (a) is about 0.5:1 to about 1.5:1.

20. The process of claim 1, wherein the molar ratio of the molybdenum compound to the succinimide product of step (a) is about 1:1.

21. The process of claim 1, wherein the alkyl or alkenyl succinimide of step (a) is a mixture of the succinimides of formula I and formula II.

22. The process of claim 21, wherein the ratio of the succinimide of formula I to the succinimide of formula II in the succinimide mixture is from about 1:1 to 10:1.

23. The process of claim 21, wherein the ratio of the succinimide of formula I to the succinimide of formula II in the succinimide mixture is at least about 4:1.

24. The process of claim 21, wherein the ratio of the succinimide of formula I to the succinimide of formula II in the succinimide mixture is about 9:1.

25. The process of claim 1, wherein the reaction temperature of step (a) is at least 90° C.

26. The process of claim 1, wherein the reaction temperature of step (a) is at least 100° C.

27. The process of claim 1, wherein the reaction temperature of step (a) is at least 120° C.

28. The process of claim 1, wherein the reaction temperature of step (a) is no greater than 140° C.

29. The process of claim 1, wherein the reaction temperature of step (a) is no greater than 135° C.

30. The process of claim 1, wherein the molybdated succinimide complex is a molybdated mono-succinimide complex.

31. The process of claim 1, wherein the molybdated succinimide complex is a molybdated bis-succinimide complex.

32. The process of claim 1, wherein the molybdated succinimide complex is a mixture of molybdated mono-succinimide complex and molybdated bis-succinimide complex.

\* \* \* \* \*